United States Patent [19]

Cullis et al.

[11] 4,185,629
[45] Jan. 29, 1980

[54] METHOD AND APPARATUS FOR PROCESSING BLOOD

[75] Inventors: Herbert M. Cullis, Silver Spring, Md.; James H. DeVries, McHenry, Ill.; David A. Lohr, Ellicott City, Md.; Rodolfo R. Rodriquez, Columbia, Md.; Michael B. Uffer, Baltimore, Md.

[73] Assignee: Baxter Travenol Laboratories, Inc., Deerfield, Ill.

[21] Appl. No.: 843,222

[22] Filed: Oct. 18, 1977

[51] Int. Cl.² .................. A61M 5/00; B04B 11/00
[52] U.S. Cl. ............................ 128/214 R; 233/19 R
[58] Field of Search ........... 128/214 R, 214 A, 214 B, 128/214 C, 214 D, 214 E, 214 F, 272; 233/19, 20, 1, 14 R (U.S. only), 27 (U.S. only), 19, 20; 210/84

[56] References Cited

U.S. PATENT DOCUMENTS

| 3,737,096 | 6/1973 | Jones et al. ..................... 233/14 R |
|---|---|---|
| 3,752,389 | 8/1973 | Nilsson ........................... 233/20 R |
| 3,957,197 | 5/1976 | Sartory et al. ................... 233/4 |

Primary Examiner—Robert W. Michell
Assistant Examiner—Thomas Wallen
Attorney, Agent, or Firm—Henry W. Collins; Paul Flattery; Thomas R. Vigil

[57] ABSTRACT

The blood processing method, and the apparatus for performing the steps of the method are utilized in separating whole blood into its components and include the steps of, or component parts of the apparatus for carrying out these steps of: pumping whole blood from a donor; passing the whole blood through a first chamber in a centrifuge device; centrifuging the whole blood in the centrifuge device to cause sedimentation of red blood cells from the whole blood in, and separation of platelet rich plasma from the whole blood in, the first chamber; pumping the separated platelet rich plasma from the first chamber and out of the centrifuge device where it is monitored and then back into the centrifuge device and through a second chamber in the centrifuge device where the platelet rich plasma is centrifuged to cause sedimentation of the platelets therein while passing the remaining blood fluid though the first chamber and back to the donor; recombining the plasma passed through the second chamber with the blood fluid passed through the first chamber for return to the donor; monitoring the platelet rich plasma outisde of the centrifuge device and sensing the presence of red blood cells in the platelet rich plasma; stopping and then reversing movement of the platelet rich plasma mixed with red blood cells when a mixture is sensed to return the mixture of platelet rich plasma mixed with red blood cells to the first chamber for separation of the blood components; adjusting the difference in volumetric flow rates of the pump for the whole blood pump and the pump for platelet rich plasma in response to the sensing of red blood cells; repeating the above steps until a desired volume of whole blood has been processed, and stopping operation of the centrifuge device and removing the second chamber with platelets therein from the apparatus.

54 Claims, 9 Drawing Figures

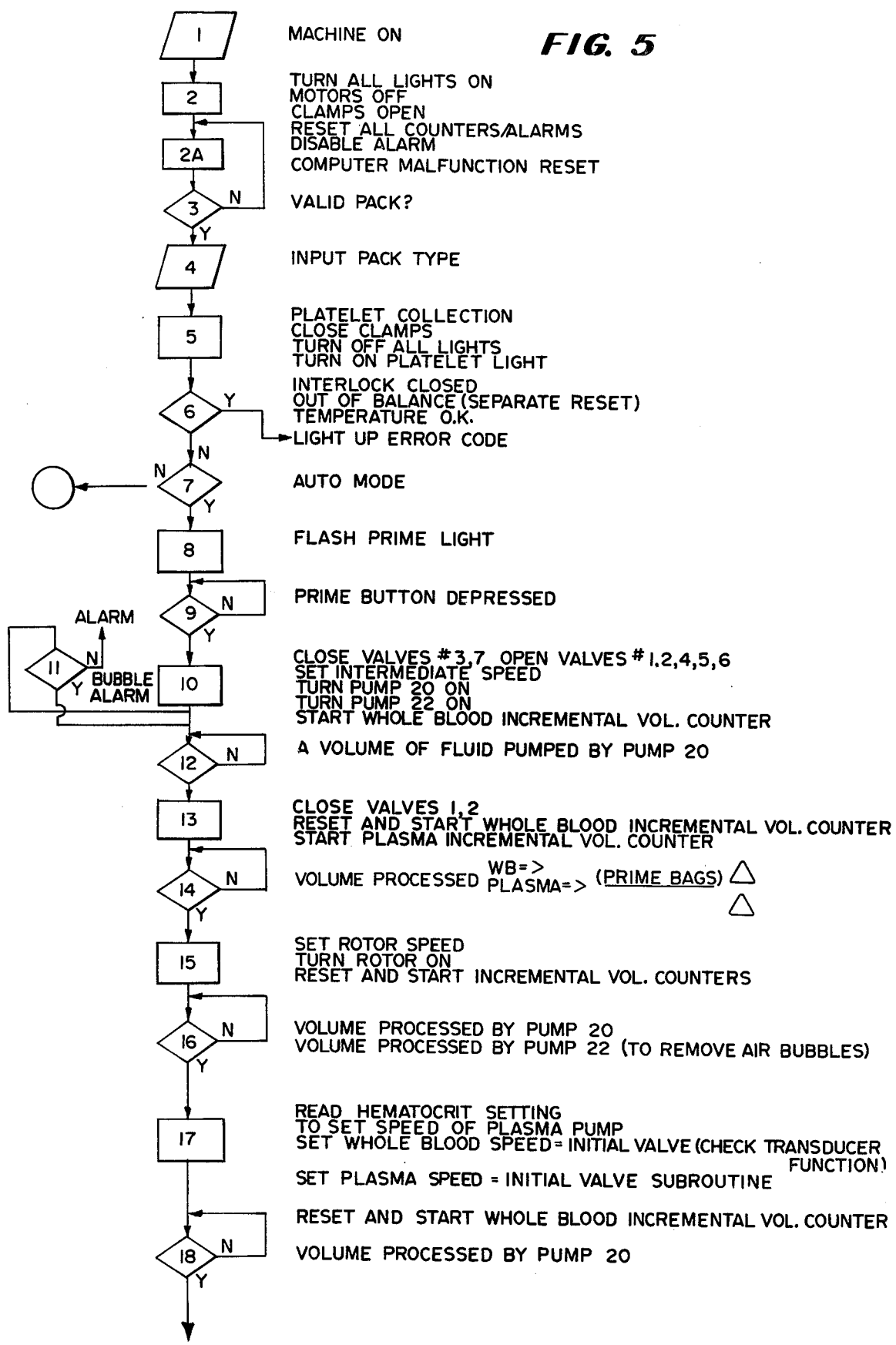

METHOD AND APPARATUS FOR PROCESSING BLOOD

CROSS REFERENCE TO RELATED APPLICATIONS

This application is related to, and incorporates herein by reference, copending application Ser. No. 843,223 Filed: Oct. 18, 1977 Entitled: MONITOR AND FLUID CIRCUIT ASSEMBLY and application Ser. No. 843,296 Filed: Oct. 18, 1977 Entitled: CENTRIFUGAL LIQUID PROCESSING SYSTEM.

BACKGROUND OF THE INVENTION

1. Field of the Invention

The present invention relates to a method and apparatus for processing whole blood and more specifically to a method and apparatus for separating whole blood into its components for collection of a desired component such as platelets.

2. Description of the Prior Art

Heretofore various methods and apparatus have been proposed for processing whole blood and separating the same into the various components thereof. Such prior art methods and apparatus have involved intervivos blood processing in which whole blood is taken from a live donor, separated within a processing system into its constituent components and a desired component is segregated for collection from the donor, followed by returning the remaining blood fluid to the donor. Typically, the blood components that are separated are plasma, red blood cells, white blood cells and platelets. As will be described in greater detail, the method and apparatus of the present invention are particularly adapted for separating platelets from whole blood. Such a method or process is commonly referred to as plateletpheresis.

Methods and apparatus for carrying our intervivos blood processing that have been utilized in the past, have typically included a separation chamber within which whole blood from a donor is subjected to a centrifugal force. This is typically accomplished in a centrifuge device. Because of differences in densities the various blood components will congregate in different zones at different radial distances from the center of rotation of the separation chamber. Then, collection ports in the chamber are utilized to remove the blood components from the various zones in the separation chamber for storage or recirculation.

Heretofore such methods and devices have required a large quantity of whole blood in order to separate the whole blood into the various components thereof. Also, such previously proposed methods and apparatus have required a significant amount of time such as from 2½ to 4 hours to obtain a desired quantity of platelets or other blood component. Also, and what is very significant, the prior art methods and apparatus have often required the almost constant attention of an operator to make certain that proper separation was being effected in the separation chamber without contamination of one blood component with another blood component such as for example, red blood cells with platelet rich plasma.

As will be described in greater detail hereinafter, the present invention differs from the previously proposed methods and apparatus by providing a method and apparatus which requires a minimum amount of time to separate blood components and collect a desired blood component such as platelets, which takes a minimum amount of whole blood from a donor in order to effect efficient separation, which is effective and efficient at separating the whole blood into its various components, particularly platelets, and which does not require the constant attention, manipulation and operation by an operator. With respect to the latter, the apparatus of the invention functions essentially automatically with very little operator intervention.

SUMMARY OF THE INVENTION

According to the invention there is provided a method for separating blood components from whole blood including the steps of: withdrawing whole blood from a donor and passing the same through a system; said passing of whole blood through the system including passing the whole blood through a first compartment for the centrifuging of the whole blood therein; centrifuging the whole blood to cause separation of the whole blood into components thereof in the first compartment; withdrawing one fluid component out of the first compartment for monitoring the one fluid component and moving that one fluid component through a second compartment for the centrifuging of the one component therein while passing the remaining blood fluid through the first compartment; centrifuging the one fluid component in the second compartment to cause sedimentation of particles therein; recombining the fluid passed through the second compartment with the blood fluid passed through the first compartment; returning the recombined blood fluid to the donor; monitoring the withdrawn one fluid component and sensing withdrawal of other components with the one fluid component; stopping and then reversing movement of the one fluid component when a mixture is sensed to return any mixture of components sensed to the first compartment for separation of the blood components therein; adjusting the difference in rates of withdrawal of whole blood and the one component in response to said sensing of a mixture of components; repeating the above steps until a desired volume of whole blood has been processed followed by isolating and removing the second compartment from the system.

Further according to the invention there is provided an apparatus for separating blood components from whole blood comprising: a centrifuge device, a first, whole blood receptacle situated in said device and having an inlet and at least a first outlet and a second outlet, said first outlet being located adjacent a zone where one blood component congregates and said second outlet being located adjacent a zone where another blood component congregates when the centrifuge device is operated, a second receptacle situated in said device and having an inlet and an outlet, means exterior of said device for withdrawing whole blood from a donor, first means coupling said withdrawing means to said first receptacle inlet, second means coupling said first outlet of said first receptacle to the donor, third means coupling said second outlet of said first receptacle to said inlet of said second receptacle, fourth means for coupling said outlet of said second receptacle to said second coupling means for recombining the one blood component with the blood fluid from said first receptacle, means for moving the one blood component from said first receptacle to said second receptacle in which particles are separated from one blood component by centrifugal force and means for monitoring the one blood component fluid flow in said third coupling means and for sensing when another blood component is present in said third coupling means, means for stopping and then reversing operation of said moving means in response to the sensing of the presence of a mixture of blood components to return the mixture to said first receptacle for separation of the blood components therein, and means for adjusting the relative rates of fluid movement of said withdrawing means and said moving means in response to the sensing of the other blood component.

BRIEF DESCRIPTION OF THE DRAWINGS

FIGS. 5, 5A and 5B comprise a block flow diagram of the operational steps performed by the microprocessor of the apparatus of the present invention.

DESCRIPTION OF THE PREFERRED EMBODIMENT

Figure 1:
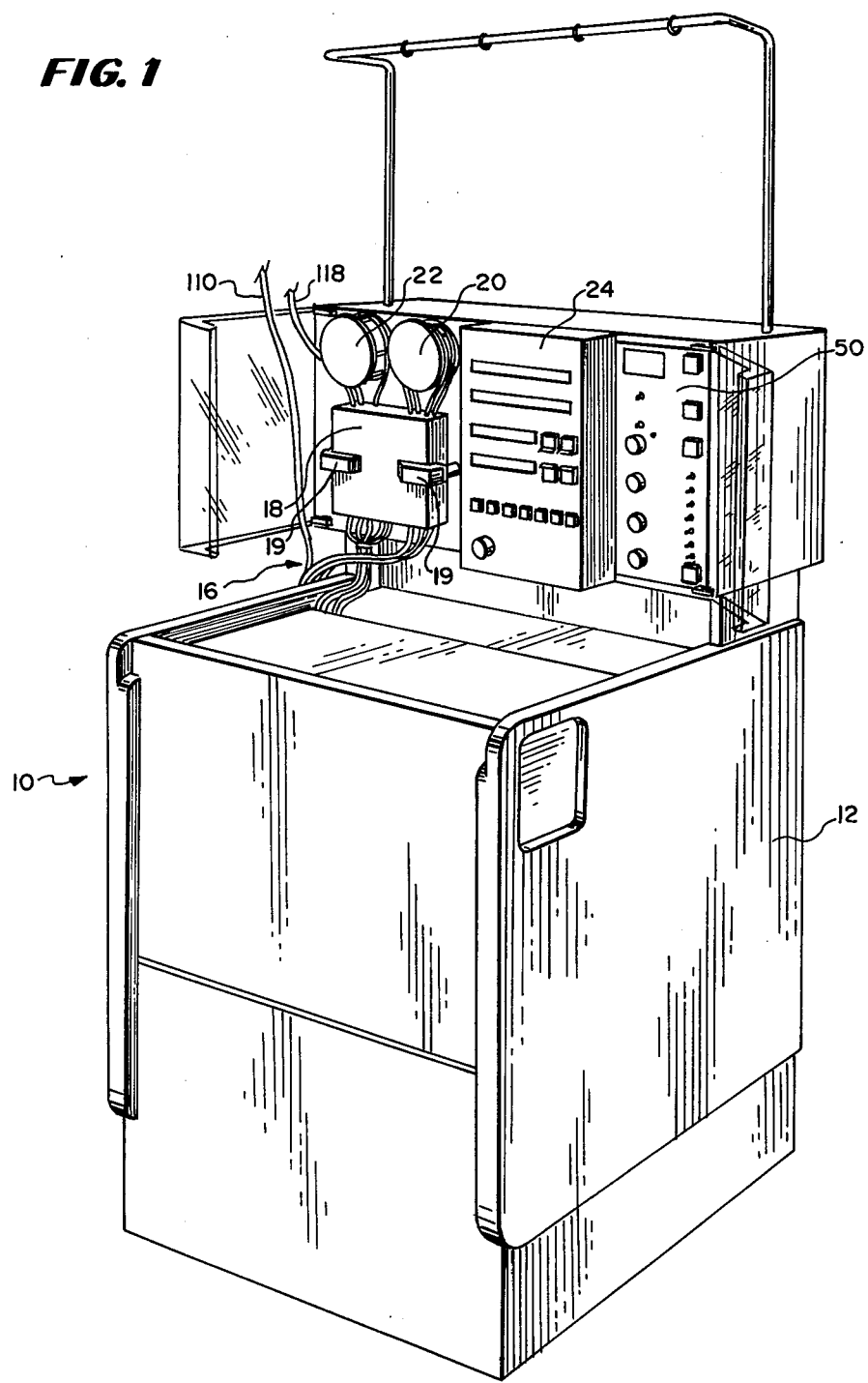
FIG. 1 is a perspective view of the apparatus of the present invention.

Referring now to the drawings in greater detail, the apparatus of the present invention is illustrated in FIG. 1 and is generally identified by the reference numeral 10. The apparatus 10 includes a cabinet 12 in which is mounted a centrifuge device hidden from view within the cabinet 12. The centrifuge device is shown schematically in FIG. 3 and identified therein by reference numeral 14. For further details of the construction and operation of the centrifuge device 14, reference is made to co-pending application, Ser. No. 843,296, filed Oct. 18, 1977, entitled: CENTRIFUGAL LIQUID PROCESSING SYSTEM, the disclosure of which application is incorporated herein by reference.

Figure 3:
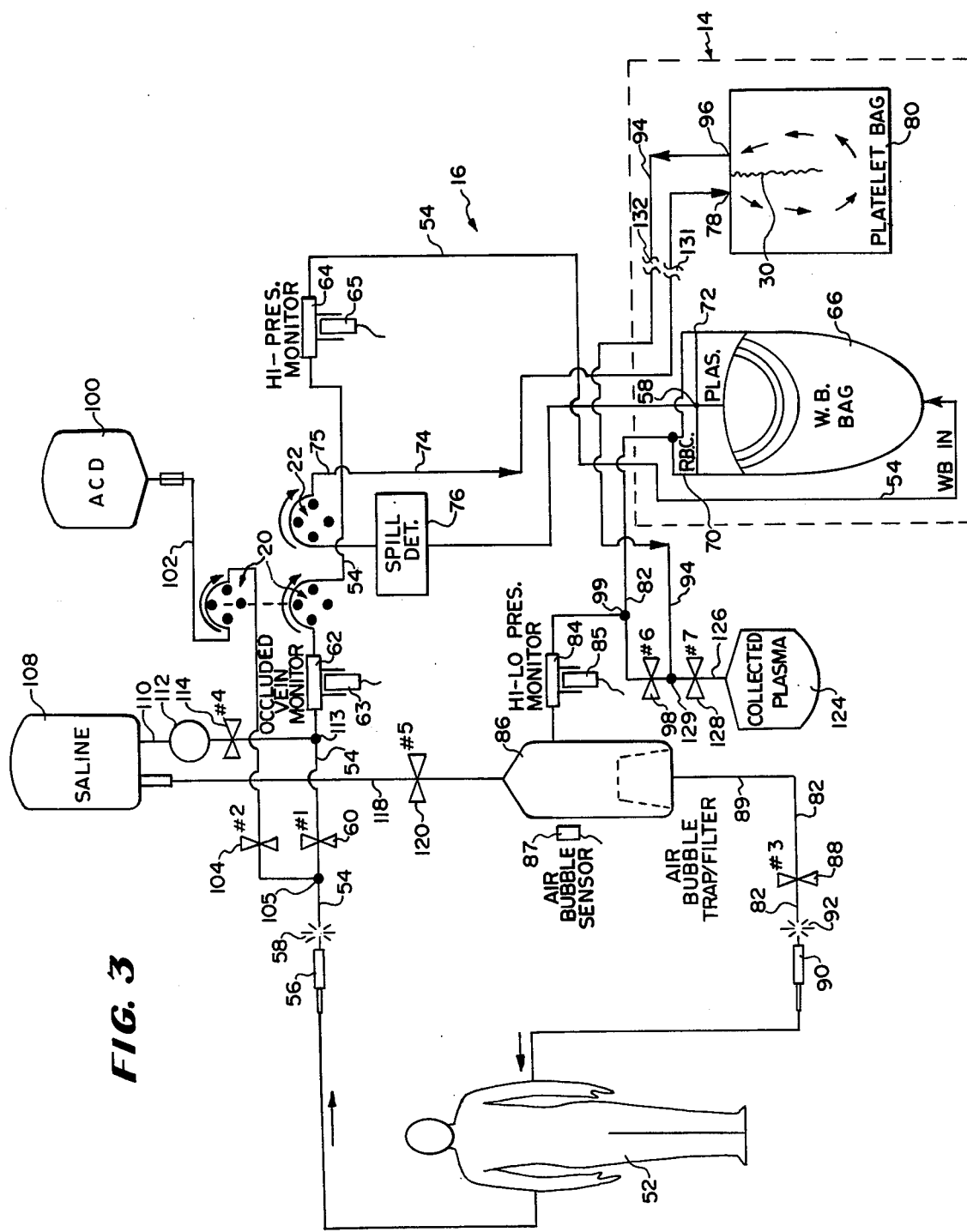
FIG. 3 is a schematic block flow diagram of the fluid circuit of the present invention.

The apparatus 10 further includes a fluid circuit generally identified by the reference number 16 in FIG. 1 and best shown schematically in FIG. 3. The fluid circuit 16 includes a plurality of flexible plastic tubings which form fluid couplings between various parts of the fluid circuit 16. These tubings are received through a holder 18 having monitor devices therein. The fluid circuit 16 of the apparatus is described hereinafter in more detail in connection with the description of FIG. 3 and for specific details of construction of the tubings of the fluid circuit 16 and of holder 18 reference is made to co-pending application, Ser. No. 843,223, entitled MONITOR AND FLUID CIRCUIT ASSEMBLY, the disclosure of which is incorporated herein by reference. The holder 18 is held in place on the apparatus 10 by pivotal clamp arms 19.

Figure 2:
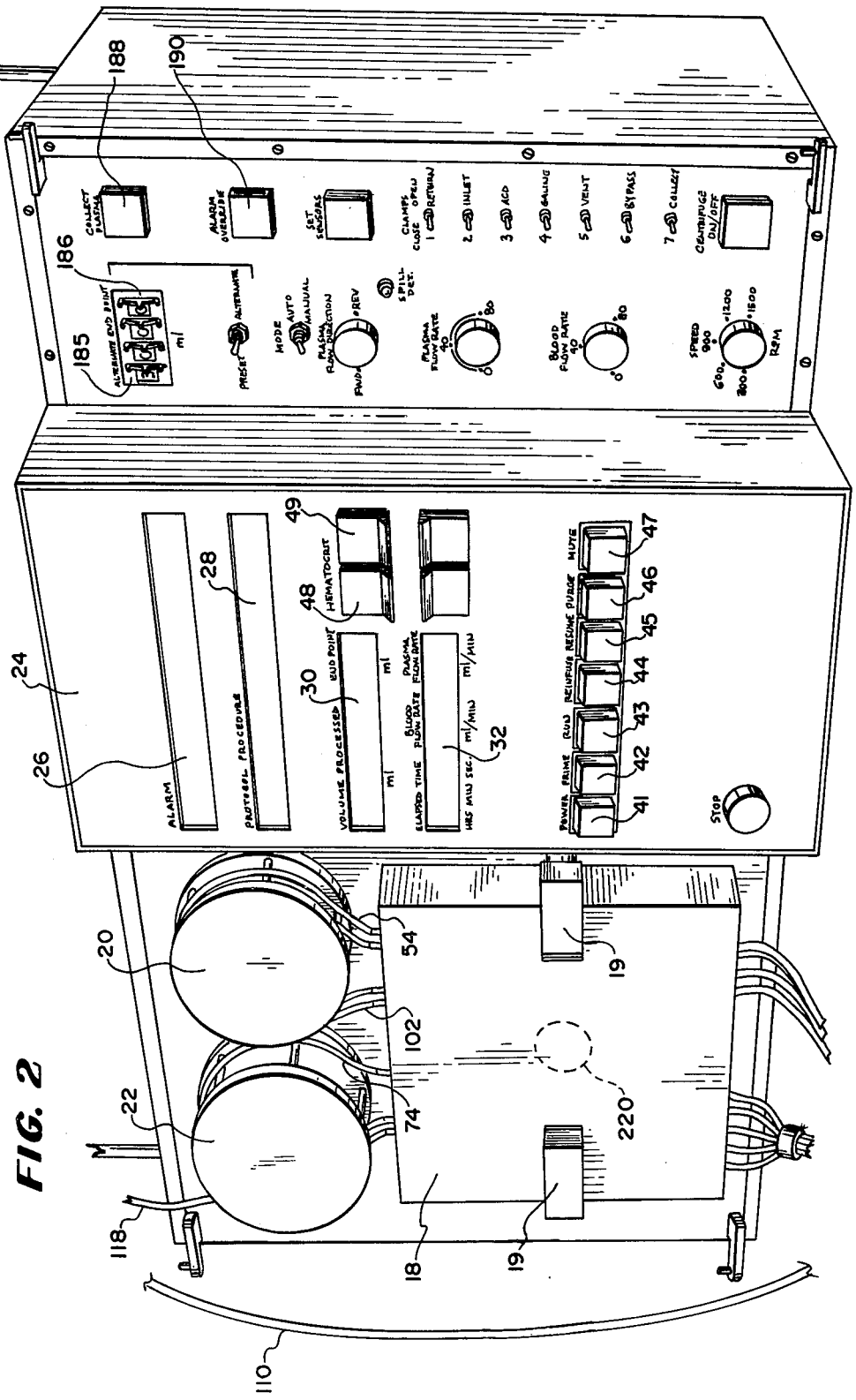
FIG. 2 is an enlarged perspective view of the upper portion of the apparatus shown in FIG. 1.

As shown in FIGS. 1 and 2, several loops of the tubings (54, 74, 102 in FIG. 3) are received over, in tight contact with, and form part of two peristaltic pumps 20 and 22. As will be described in greater detail hereinafter, the pump 20 is referred to as a first or whole blood pump and the pump 22 is referred to as a second or plasma pump. The whole blood pump 20 is utilized for withdrawing whole blood from a donor whereas the plasma pump 22 is utilized to move plasma from one chamber to another chamber within the centrifuge device 14 (FIG. 3).

The apparatus 10 also includes a display panel 24 including several windows for indicating information useful to an operator. In this respect, an alarm window 26 indicates a malfunction of the apparatus 10 or a condition occurring within the fluid circuit 16 of the apparatus 10. Also there is a window 28 indicating the blood component which is being collected, a window 30 indicating volume processed and end point and a window 32 indicating the elapsed time of operation of the apparatus, the flow rate of the whole blood and the flow rate of platelet rich plasma.

A number of push buttons 41–47 are provided for controlling various phases of operation of the apparatus 10, as well as windows 48 and 49 on the display panel 24 for indicating the hematocrit of the donor, which data is fed into the control circuitry of the apparatus to be described hereinafter in connection with the description of FIGS. 4, 5, 5A and 5B.

Additionally, the apparatus 10 includes a manual control panel 50 which, as best shown in FIG. 2, includes a plurality of knobs and switches for manual operation of the apparatus 10. The legends on the manual control panel 50 generally identify the various toggle switches and push button switches, the purpose of which will become apparent from the detailed description of the operation of the apparatus 10 set forth below.

Referring now to FIG. 3 there is illustrated therein a block schematic diagram of the fluid circuit 16 of the apparatus 10 of the present invention. As shown, the circuit 16 includes a first fluid coupling or tubing 54 adapted to be coupled to a vein in one arm of a donor 52 by means of a hypodermic needle 56 which is injected into the arm. If desired a fluid clamp 58 (shown schematically) can be provided on the tubing 54. The first tubing 54 has associated therewith a solenoid operated clamp 60 forming valve #1. The tubing 54 then has series coupled thereto an occluded vein monitor device 62 with an associated sensor 63. Then, the first tubing 54 extends over and forms part of the peristaltic pump 20 and is series coupled to a high pressure monitor device 64 with an associated sensor 65. From the monitor device 64 the first tubing 54 extends into the centrifuge device 14 and to the bottom inlet of a first compartment or receptacle 66 which is identified as a whole blood bag and which defines therein a whole blood separation chamber in which blood is separated into its components.

The receptacle 66 has a first outlet 68 at the center thereof adjacent a zone in the receptacle 66 where platelet rich plasma congregates. Receptacle 66 also has two outlets 70 and 72 at the upper corners thereof where red blood cells congregate. Outlet 68 provides not only an outlet for platelet rich plasma but also a return inlet for platelet rich plasma which is "contaminated" (mixed) with red blood cells when there is a spillover of red blood cells out of outlet 68.

The outlet 68 of the first receptacle 66 is coupled by a second fluid coupling or tubing 74 to a loop 75 thereof located exterior of the centrifuge device 14 and which loop 75 extends about and forms part of the peristaltic pump 22. Also, positioned adjacent a light transmitting section of the loop 75 which extends out of the centrifuge device 14 is a spill detector device 76 which is an optical sensor for sensing a spillover of red blood cells mixed with platelet rich plasma out of outlet 68. The device 76 includes a light emitting diode (LED), such as an infra red LED sold by Texas Instruments under type No. TIL32 and a phototransistor, such as a phototransistor sold by Texas Instruments under type No. TIL 81. The second tubing 74 then goes back into the centrifuge device 14 and is coupled to an inlet 78 of a second compartment or receptacle 80 which is identified as a platelet bag defining a chamber therein in which platelets are separated from plasma.

A third fluid coupling or tubing 82 is connected to the outlets 70 and 72 of the receptacle 66 for returning the red blood fluid to the donor through a high/low pressure monitor device 84 with associated sensor 85 and an air bubble trap/filter 86 and associated air bubble sensor 87 which monitor device 84 and filter 86 are coupled in series in the third tubing 82. Also another solenoid calmp 88 is associated with a portion 89 of the tubing 82 coming out of the air bubble trap/filter 86 and forms valve #3. The sensor 87 can be optical or ultrasonic.

The end of third tubing 82 is connected to a hypodermic needle 90 for injection into the other arm of the donor and, if desired, a fluid clamp 92 (shown schematically) can be provided on tubing 82 ahead of the needle 90.

The fluid circuit 16 further includes a fourth fluid coupling or tubing 94 which is coupled between an outlet 96 of the second receptacle 80 through a solenoid operated clamp 98 forming valve #6 and a junction 99 with the third tubing 82.

The fluid circuit 16 also includes a container 100 of anti-coagulant such as Acid Citrose Dextrose (ACD) which is coupled by a fifth fluid coupling or tubing 102 about (and forming part of) the peristaltic pump 20 and through a solenoid operated clamp 104 defining valve #2 to a junction 105 with the first tubing 54 between the needle 56 and valve #1. The container 100 is typically a flexible plastic container.

With this arrangement of the first tubing 54 and the fifth tubing 102 passing over the same peristaltic pump 20, the mixing of anti-coagulant with whole blood and the withdrawing of whole blood from the donor is achieved essentially simultaneously. Also, the ratio of the cross-sectional area of the interior of the tubing 54 to the cross-sectional area of the interior of the tubing 102 is chosen to obtain a desired mixture of anti-coagulant to whole blood. This ratio is preferably 8 to 1 thereby to obtain an 8 to 1 ratio of whole blood to anti-coagulant.

The apparatus 10 and fluid circuit 16 further include a container 108 of saline solution which is connected by means of a sixth coupling or tubing 110 through a drip chamber 112 and a solenoid operated clamp 114 defining a valve #4 to the first tubing 54 at a junction 115 between solenoid operated clamp 60 and the occluded vein monitor device 62. The container 108 of saline solution is also coupled by means of a seventh fluid coupling or tubing 118 through a solenoid clamp 120 forming valve #5 to the top of the air bubble trap/filter 86. The container 108 is typically a flexible plastic container.

The apparatus 10 and the fluid circuit 16 thereof further include a third receptacle or compartment 124 located outside of the centrifuge device 14 for collecting plasma. This receptacle 124 is coupled by an eighth coupling or tubing 126 through a solenoid operated clamp 128 forming solenoid valve #7 to the fourth tubing 94 at junction 129.

The pressure monitor devices 62, 64 and 84 each include a flow through chamber series connected in the associated tubing 54 or 85 and an air filled closed chamber having a flexible diaphragm forming part of one wall of the flow through chamber and an outer wall which is situated adjacent the associated sensor 63, 65 or 85 which are pressure transducers and which senses changes in pressure on the outer wall.

The monitor devices 63, 65 or 85 and air bubble filter/trap 86 are mounted in holder 18.

The operation of the apparatus 10 for processing whole blood through the fluid circuit 16 will now be briefly described with reference to FIG. 3. Also, although the operation of the apparatus 10 will now be described in connection with the collection of platelets, the apparatus 10 can be used for the collection of another blood component, e.g., red blood cells or white blood cells.

First of all, a donor is chosen who will be a healthy person donating platelets and who will be treated much like a blood donor. When the apparatus 10 is ready, two venipunctures will be made, one in each arm, with needles 56 and 90.

Valve #1 is opened first to allow saline to purge the input needle 56 prior to injection in the donor. Then valves #1, #2, #5 and #7 are closed. Valves #3, #4 and #6 are open.

Then, saline is pumped by the first pump 20 through the fluid circuit 16 until no more air bubbles are sensed by the air bubble sensor 87, i.e., until saline is sensed. Next, the second pump 22 is started and saline is pumped through the platelet receptacle 80. Since the centrifuge device 14 is not running at this time, the receptacles 66 and 80 are not filled to capacity. Air is expelled through the needle 90.

After a short time, e.g., one to five minutes the platelet receptacle/bag 80 will be filled, all air expelled and saline fills the entire system, i.e., fluid circuit 16 up to valve #3. When saline is sensed by detector 87, valve #3 is closed and valve #5 is opened. After a period of recirculation of saline, pumps 20 and 22 are stopped and valve #3 is opened.

Parenthetically, during this priming operation, the air bubble sensor 87 is checked when air bubbles are flowing through the air bubble trap/filter 86 to make sure that sensor 87 is working properly and then later, sensor 87 is checked to make sure there are no more bubbles after the system is filled with saline.

Now the needles 56 and 90 are inserted into the arms of the donor 52 and valves #1, #2, #5 and #6 are open and valves #3 and #7 are closed.

With the needles 56 and 90 connected to the veins of a donor and the system full of saline, the pumps 20 and 22 are started and whole blood is pumped into the system and into the centrifuge device 14.

It will be noted that the tubings 54, 74, 82 and 94 extending into the centrifuge device 14 may be combined in an umbilicus which is rotated at a speed ½ the speed of the centrifuge device so that twisting is avoided and no fluid seals are required. This arrangement and operation of the centrifuge device 14 is more fully described in the co-pending application entitled:

CENTRIFUGAL LIQUID PROCESSING SYSTEM, referred to above.

When approximately 120 milliliters of whole blood has been pumped into the fluid circuit 16, most of the saline solution will have been pumped back into the container 108. Valve #3 is now opened so that processed blood fluid mixed with some saline solution can now be returned to the donor.

Figure 4:
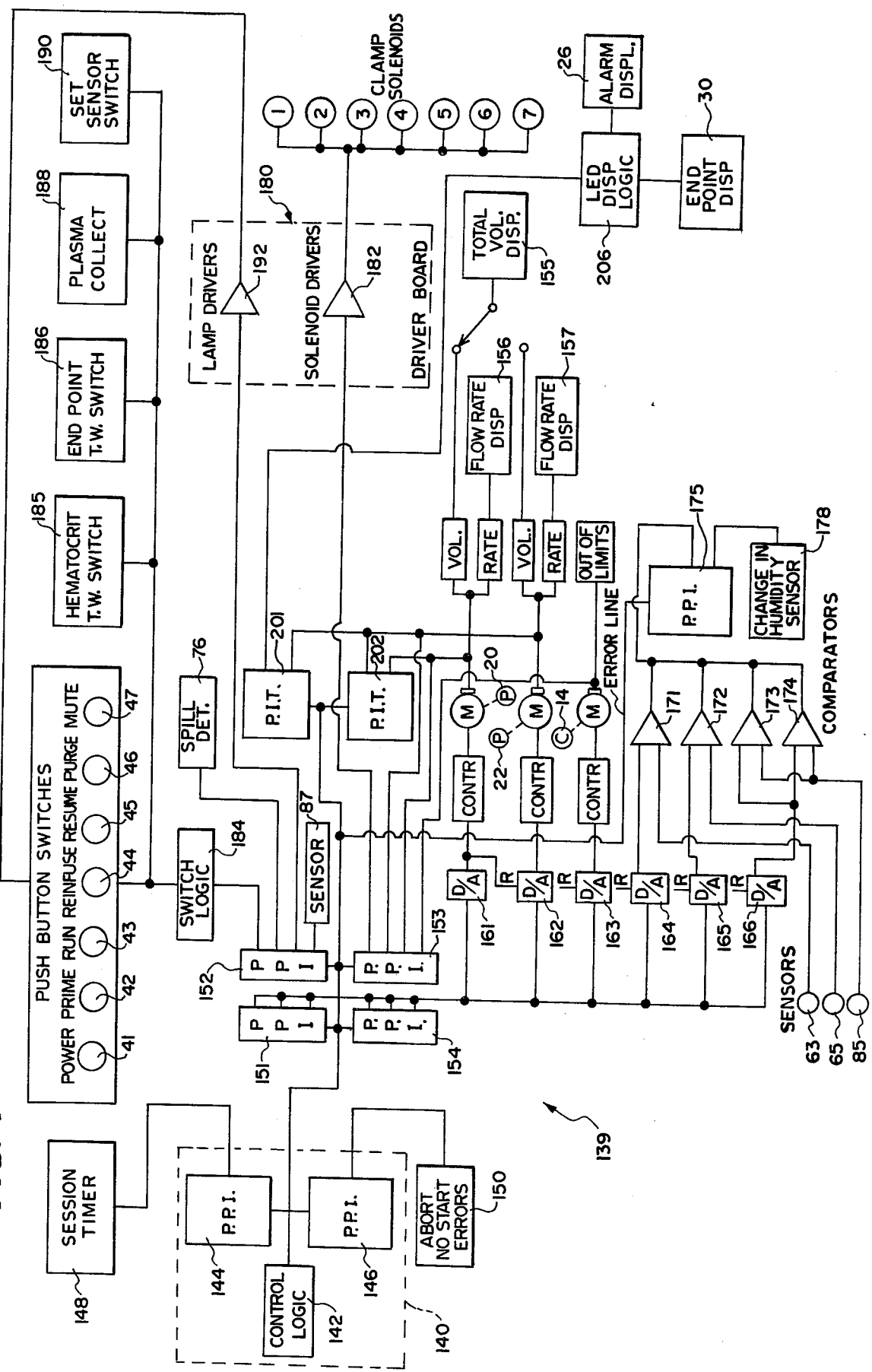
FIG. 4 is a block circuit diagram of the microprocessor and associated electrical circuitry of the apparatus of the present invention.

Also, if the plasma collect button 188 in FIG. 4 had been pushed, valve #6 is closed and valve #7 opened. As will be described hereinafter in more detail in connection with the description of FIGS. 4, 5, 5A and 5B, the control circuitry (139 in FIG. 4) of the apparatus 10 will determine when the desired amount of plasma has been collected while whole blood is being processed through the fluid circuit 16 and then will cause closing of valve #7 and opening of valve #6.

After starting pumps 20 and 22 no further operator attention is required until the end of the run.

Typically, the whole blood is withdrawn from the donor at a volumetric rate of between 15 and 50 milliliters per minute and through empirical tests it has been found that a whole blood rate of withdrawal of approximately 30±5 milliliters per minute provides the best results. In this respect, a proposed operating procedure for the apparatus 10 is to start the volumetric rate of withdrawal, i.e., the speed of the peristaltic pump 20 at a rate of 26 milliliters per minute.

As the whole blood is being drawn into the fluid circuit 16 and into the separation chamber in the receptacle 66, the centrifugal force acting on the receptacle 66 causes separation of the components of the whole blood. In this respect, platelet rich plasma congregate in a zone at the top of the receptacle 66 adjacent to outlet 68 and red blood cells congregate at the upper corners of the receptacle 66 adjacent outlets 70 and 72. This is achieved by the particular construction and orientation of the receptacle 66 which is described in more detail in the co-pending application entitled: CENTRIFUGAL LIQUID PROCESSING SYSTEM, referred to above.

The centrifuge device can be rotated at any one of several speeds of rotation from 0 to 1600 RPM. In a working example of the apparatus 10, a speed of 1400 RPM has been found to work very well. The speed of rotation of the centrifuge device 14 must be, of course, correlated with the distance of the two receptacles 66 and 80 from the axis of rotation of the centrifuge device in order to obtain a desired "g" force on the blood fluid in the respective receptacles 66 and 80. In this respect, it has been found that a "g" force of between 150 and 600 "g's" provides good results, that is to say good separation of blood into its components. In a working example of the apparatus 10, the centrifuging takes place in the first and second receptacles 66 and 80 at approximately 285 "g's".

In the processing of whole blood it has been found best to process about 3 liters of blood at any one time. Accordingly, the controls for the apparatus 10 are set to process 3 liters of whole blood from the donor.

Figure 6:
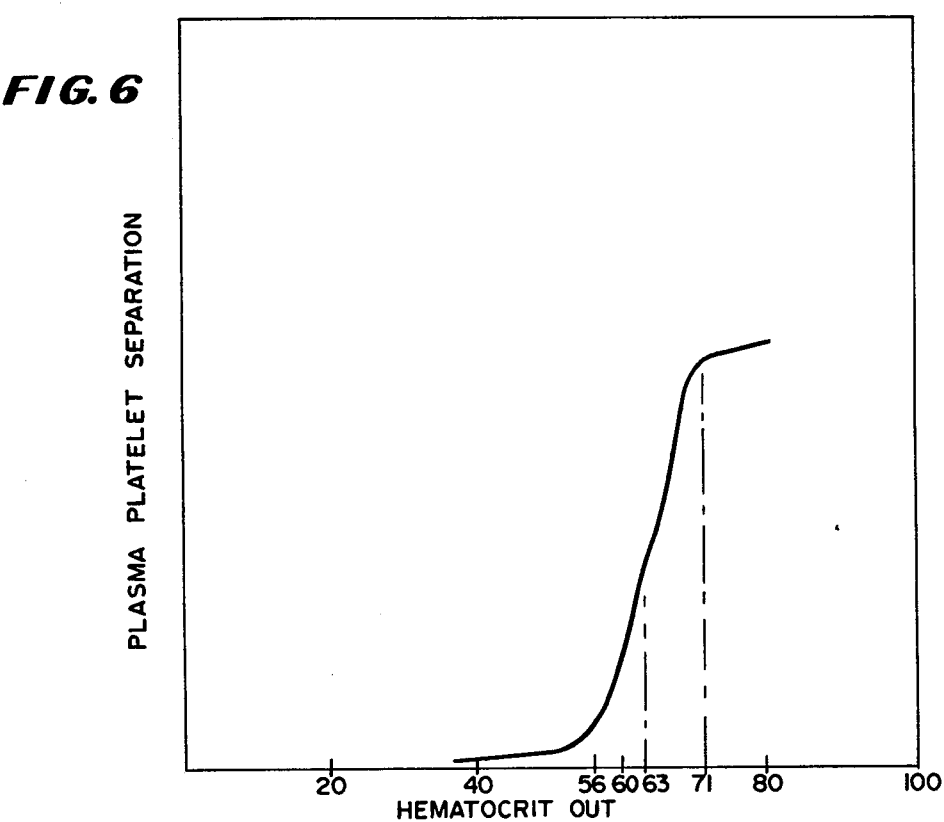
FIG. 6 is a graph depicting the efficiency of plasma and platelet separation from whole blood as a function of the hematocrit of the whole blood that exits from a blood separation chamber of the apparatus.

In light of the texture, size and number of particles in the blood, namely, red blood cells, white blood cells and platelets, whole blood does not strictly obey the various physical chemistry and fluid dynamic laws. Accordingly, the various operating parameters described above and to be described below have been determined more or less empirically. In this respect, and with reference to FIG. 6 it has been found that the efficiency of separation of plasma rich in platelets, referred to as platelet rich plasma, from the remainder of the whole blood in the receptacle 66 begins at a point when the hemotocrit of the red blood cell rich blood fluid out of the outlets 70 and 72 from receptacle 66 is approximately 56. Then, essentially 50% effectiveness of separation is obtained when the hematocrit out is 63. Finally, close to 100% effective and efficient separation of platelet rich plasma from the whole blood occurs when the hematocrit out is roughly 71.

With this relationship determined empirically, 285 "g's" on the first and second receptacles 66 and 80, provides a hematocrit out of approximately 70 and efficient separation of platelet rich plasma from whole blood. From the slope of the middle portion of the curve shown in FIG. 6 it is determined that the ratio of the rates of withdrawal of whole blood and platelet rich plasma to obtain efficient separation should be caused to approach the following formula:

$$\frac{V_{BI}}{V_{BI} - V_{PRP}} = \frac{\text{HEMATOCRIT}_{(BLOOD\ FLUID\ OUT)}}{\text{HEMATOCRIT}_{(BLOOD\ IN)}}$$

where:
$V_{BI}$ = volumetric flow in milliliters per minute of whole blood into the fluid circuit 16,
$V_{PRP}$ = volumetric flow in milliliters per minute of platelet rich plasma withdrawn from the first receptacle 66,
HEMATOCRIT$_{(BLOOD\ FLUID\ OUT)}$ = concentration of red blood cells (by volume) per milliliter of blood fluid passing out of the first receptacle,
HEMATOCRIT$_{(BLOOD\ IN)}$ = concentration of red blood cells (by volume) per milliliter of fluid of the whole blood in.

Figure 7:
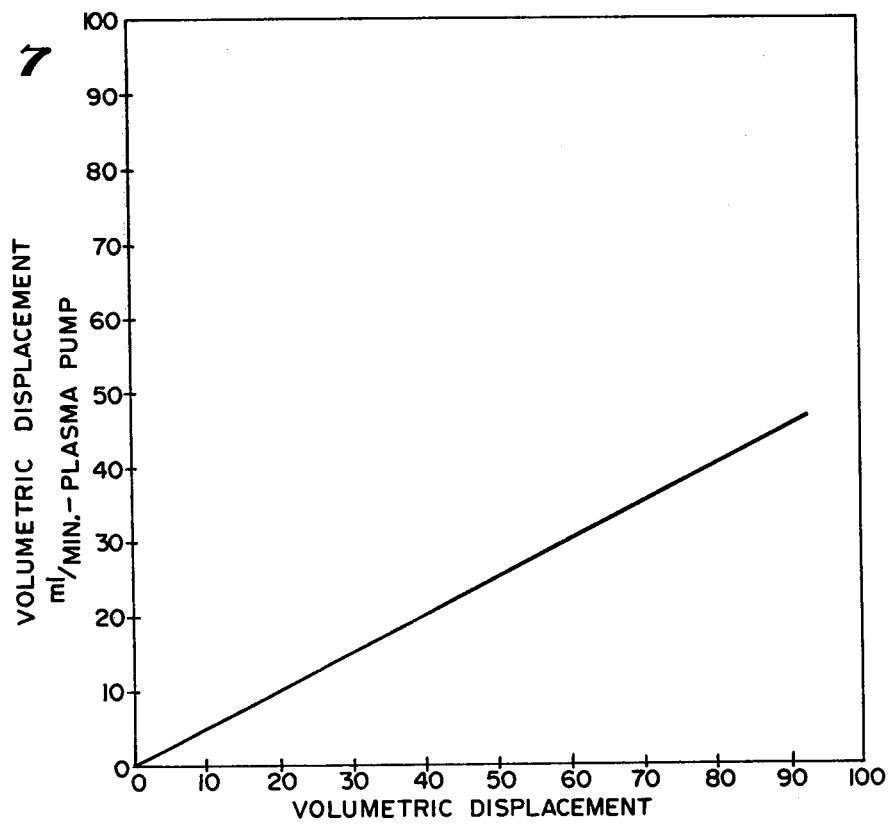
FIG. 7 is a graph showing a desired relationship between the volumetric displacement of a first pump which withdraws blood from the donor relative to the volumetric displacement of a second pump which withdraws platelet rich plasma from a zone in the blood separation chamber.

With these relationships, and knowing that the typical hematocrit of the donor is 40 one can insert into the above formula the hematocrits of 40 and 70 and obtain a ratio of approximately 0.43, i.e., the rate of pumping of the platelet rich plasma out of the receptacle 80 should be at roughly 43% of the rate of pumping of whole blood into the receptacle 66. In actual practice, however, this ratio will vary. One ratio of the volumetric displacements of the peristaltic pumps 20 and 22 which has been found to provide good results is 13:25 and is shown in FIG. 7. In one procedure for the operation of the apparatus 10 the volumetric rate of the platelet rich plasma pump 22 is started at a rate which is (1-hematocrit (WHOLE BLOOD IN))×$V_{BI}$. Since the hematocrit of the whole blood is roughly 40 this provides a starting speed for pump 22 which is roughly 60% of the speed of pump 20. As stated above, in one working example of the apparatus 10, the pump 20 is started at a speed which yields 26 milliliters per minute volumetric displacement. This ratio or relationship is maintained while the volumetric displacement of pump 20 is increased 1 milliliter per minute after each 120 milliliters of whole blood, has been processed through the fluid circuit 16 without a spillover of red blood cells. However, when a spillover of red blood cells from the receptacle 66 is sensed by the spill detector device 76, pump 22 is stopped and then reversed to return the mixture of platelet rich plasma and red blood cells to receptacle 66. Then the speed of the first pump 20 is decreased by one milliliter per minute and the speed of pump 22 is changed proportionately. Both pumps are then run in the normal direction (forward) until another 120 milliliters of whole blood is processed without a spillover. If a spillover is not detected by the device 76 the speed of the second pump 22 is then increased by 0.25 milliliters per minute for each 120 milliliters of blood processed without a spillover until a spillover is detected. Then, when a spillover is detected, the pump 22 is again stopped and reversed to return the spillover mixture to receptacle 66. Next, the volumetric displacement of the second pump 22 is decreased by 0.25 milliliters per minute and the pump 22 speed is reversed back to forward speed. This process is repeated until the end point is reached. By the end point is meant that the processing of approximately 3 liters of whole blood has been completed.

Operated in the above manner, the apparatus 10 provides a highly efficient and effective separation of platelet rich plasma from whole blood.

Referring again to FIG. 3, the platelet rich plasma which is withdrawn from the receptacle 66 is passed through the platelet receptacle or bag 80. In view of the centrifugal force acting on the bag 80, platelet sedimentation on the side of the bag 80 takes place while plasma flows through the bag 80. This flow is enhanced by pinching the bag 80 in the center thereof as indicated by the wavy line 130 in FIG. 3. This results in a flow of plasma through the bag or receptacle 80 in the manner indicated by the arrows shown in FIG. 3.

The plasma that exists from the bag 80 flows through the tubing 94 and recombines at the junction 99 with the red blood cell rich blood fluid flowing through the tubing 82. The recombined platelet poor blood is then passed through the high/low pressure monitor 84 and air bubble trap/filter 86 and back into the donor 52 through the needle 90.

Once a desired amount of whole blood, i.e., 3 liters of whole blood, has been processed, valves #1 and #2 are closed and valve #4 is opened to allow saline to flow into the system, i.e., fluid circuit 16. The saline will then purge the remaining amount of blood in the fluid circuit 16 and push it back into the donor. Then after a sufficient amount of saline has been pumped into the system the centrifuge device 14 is stopped. About 3 milliliters of blood fluid is left in the system and can be returned to the donor by allowing a short overrun of the pump 20. The cabinet 12 now can be opened to sever tubings 74 and 94 such as with a heating element as indicated by breaks 131 and 132 shown in FIG. 3. The sealed platelet receptacle/bag 80 with a minimum of plasma therein is taken out of the centrifuge 14 and stored for use.

The sequence of operation steps of the apparatus 10 are controlled by control circuitry 139 (FIG. 4) including a microprocessor or computer generally identified by reference numeral 140 in FIG. 4 and associated electronic circuitry also illustrated in FIG. 4. A more specific detailed description of the sequence of the operational steps of the microprocessor 140 and associated circuitry will be described hereinafter in connection with the description of FIGS. 5, 5A and 5B.

As shown in FIG. 4 the microprocessor 140 includes control logic circuitry 142 and at least two programmable peripheral interface chips (PPI) 144 and 146. In a working example of the apparatus 10, the microprocessor was an Intel Corporation 80/10 microprocessor and the chips carried Intel part number P8255. Coupled to the microprocessor 140 is a session timer 148 for timing the operation of the apparatus 10 and an error sensor control circuit generally identified schematically with reference numeral 150. This circuit checks for certain conditions and aborts operation of the apparatus 10 if these conditions exist, such as overtemperature of the system or motors running away. The output of the microprocessor 140 is coupled via multiple conductors to four programmable peripheral interface chips (PPI) 151–153 such as those sold under Intel Corporation part number P8255. As shown, the programmable peripheral interface chips 151 and 154 have multiple line outputs which are coupled to respective ones of a series of digital to analog converters 161–166 hereinafter referred to as D/A's. Also although only single line conductors are shown most of these lines represent multiple conductors.

As shown the D/A 161 controls a motor control for a motor which operates the pump 20. A motor speed sensor is coupled, as shown, to a volume determining device and a rate determining device and also to an input of the programmable peripheral interface chip 153 coupled to the microprocessor which determines and controls the speed of the pump 20. Similarly D/A 162 operates a control for a motor which operates the second pump 22. Again a motor speed sensor for determining the speed of the pump 22 is coupled to a volume determining device and a rate determining device. Also, the output from the motor speed sensor is coupled to another input of the programmable peripheral interface chip 153. Additionally, the rate and volume determining devices are connected to display circuitry 155, 156 and 157 which causes displays to appear in the windows 30 and 32 on the panel 24 shown in FIG. 2. The D/A 163 operates a motor control for the motor which rotates the centrifuge device 14. A motor speed sensor for sensing overrunning of the centrifuge device 14 is coupled to the motor and to an "Out of Limits" sensor as well as to another input of the programmable peripheral interface chip 153.

The D/A 164 is connected to a comparator 171 which is also connected to the sensor 63. The D/A 165 is connected to a comparator 172 which is also connected to the sensor 65. Similarly the D/A 166 is connected to a comparator 173 and to a comparator 174 and all the comparators are connected to a programmable peripheral interface chip (PPI) 175. This programmable peripheral interface chip 175 has an error line conductor(s) which is (are) coupled to the microprocessor 140 as shown. This programmable peripheral interface chip 175 is utilized to process information on the pressure sensed by the sensors 63, 65 and 85 and to indicate to the microprocessor 140 what pressure is being sensed. Also, a "change in humidity sensor" 178 is coupled to an input of the programmable peripheral interface chip 175. This humidity sensor is located within the centrifuge device 14 and when there is a break in the fluid circuit 16, the humidity within the device 14 immediately goes up and this is sensed by the sensor 178.

Returning to the first four chips 151–153, outputs of the chip 153 are also coupled to a driver board 180 and more specifically to a solenoid driver amplifier 182 the output of which is connected to the clamp solenoids for operating the clamps 60, 104, 88, 114, 120, 98 and 128 (valves #1, #2, #3, #4, #5, #6, and #7).

Outputs of the programmable peripheral interface chip 152 are coupled to a switch logic circuit 184 which is coupled in turn to push button switches 41–47, a hematocrit setting thumbwheel switch 185, an end point thumbwheel switch 186, a plasma collect switch 188 and a set sensor switch 190.

An output of the programmable peripheral interface chip 152 is also coupled to the spill detector device 76 and to the driver board 180 and more specifically to a lamp driver amplifier 192 for controlling on, off or flashing of the lamps associated with the switches 41–47.

The control circuitry 139 further includes two programmable interval timer chips (PIT) 201 and 202 sold by Intel Corporation under part number P8253. These PIT chips 201 and 202 are coupled to the microprocessor 140. Outputs of the PIT chips 201 and 202 are coupled to the motor speed sensors. The PIT chip 201 also has outputs coupled to light emitting diode (LED) display logic circuitry 206 which includes LED's located at windows 26 and 30.

Figure 5A:
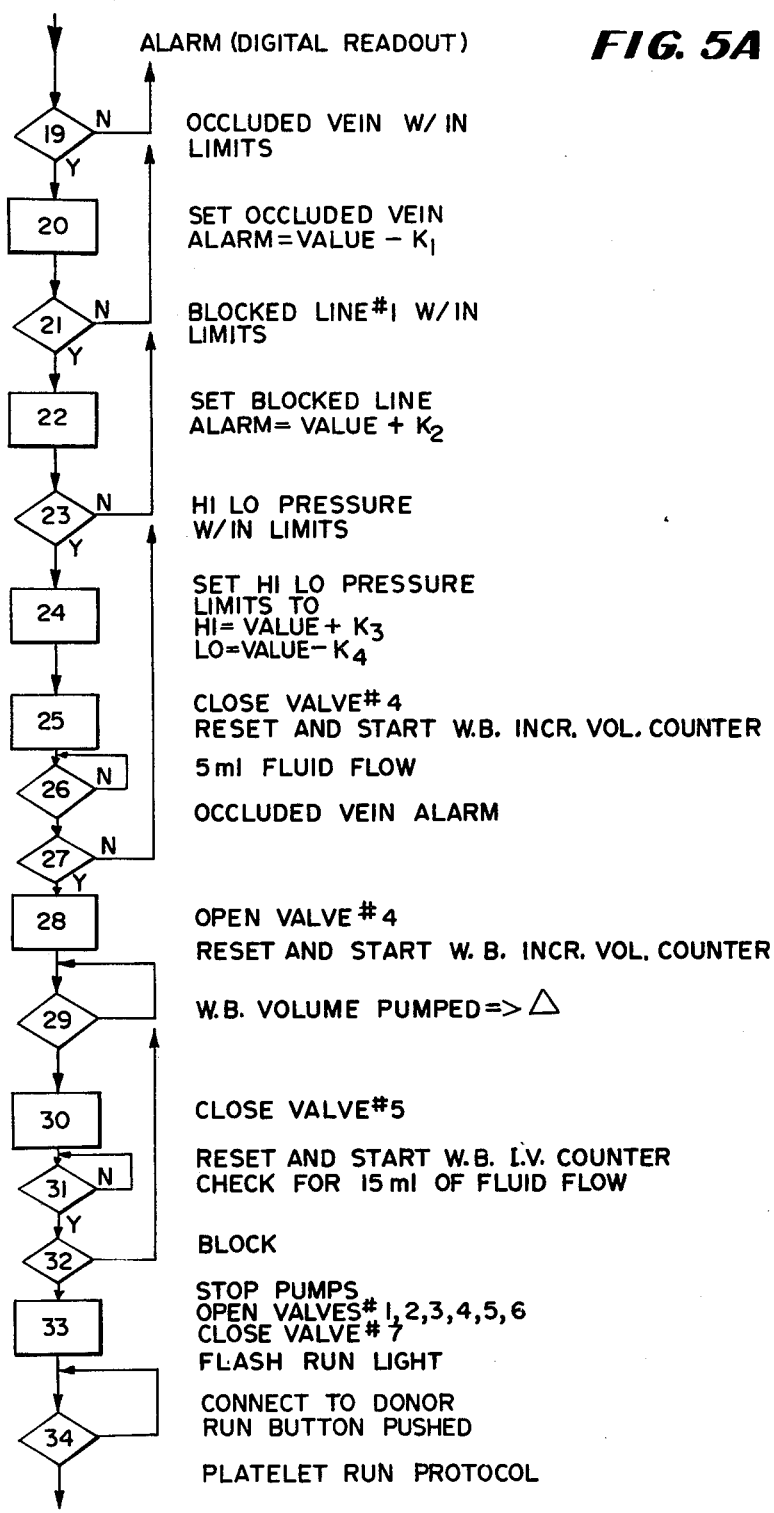
Figure 5B:
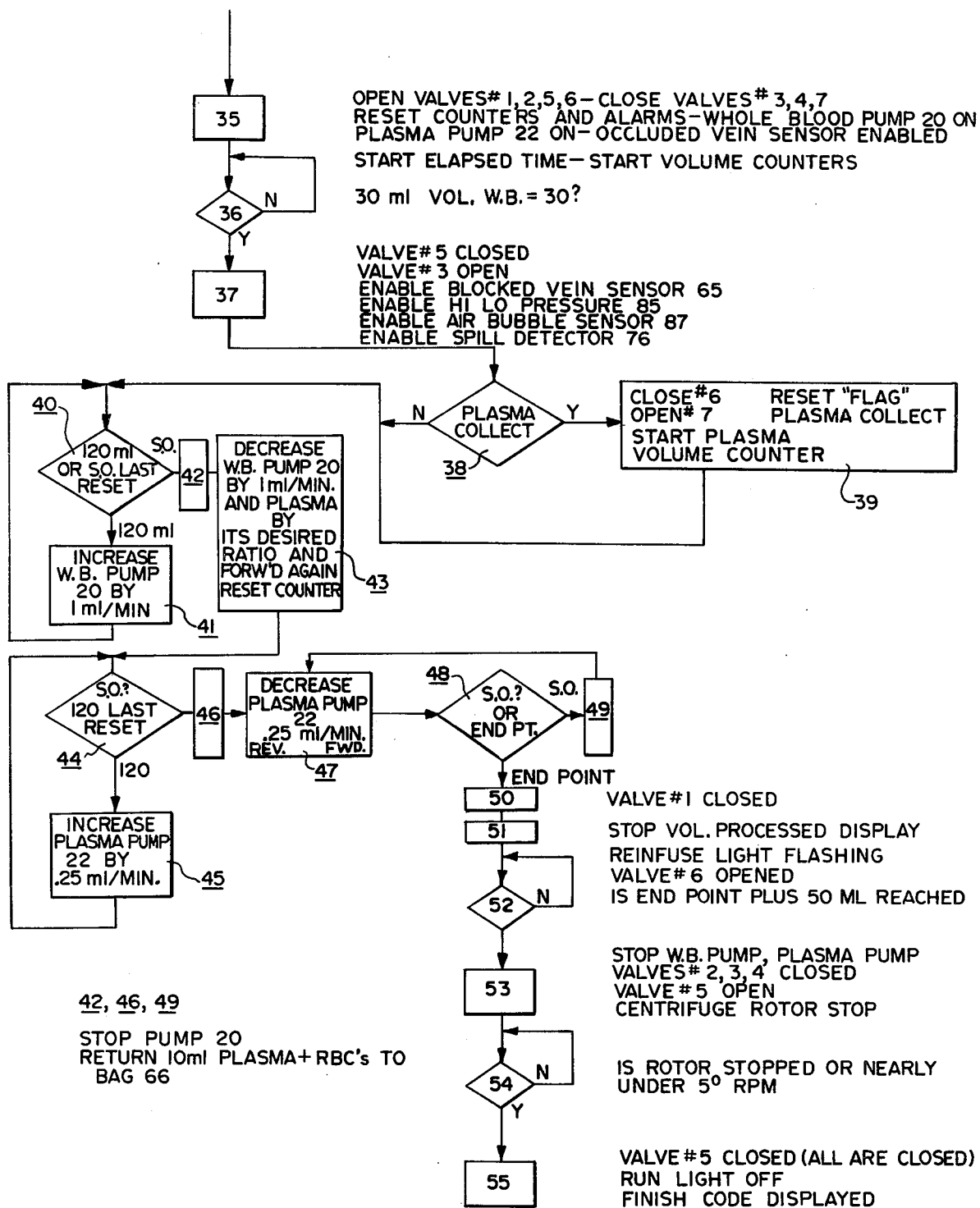

The operation of the control circuitry 139 and more specifically the operation of the microprocessor 140 will now be described in connection with one protocol, program, or operational step sequence set forth in FIGS. 5, 5A, and 5B. Also, it will be understood that the circuit connections shown in FIG. 4 and connections (programming) of the microprocessor 140 are such as will provide the following sequence of operational steps of the apparatus 10, the steps being numbered 1 to 55. Each "rectangular" step is an operation step, i.e., something occurs or has occurred and each "rhombus" step is a check or question step to see if something has or has not occurred or exists or does not exit.

The sequence of operation steps of the one protocol or program worked out for a working example of the apparatus 10 are as follows:

STEP 1

First the machine, i.e., apparatus 10, is turned on and the microprocessor 140 is turned on. This is a manual step performed by operating push button 41.

STEP 2

All lights are now turned on, the motors are off, the clamps are open, all counters and alarms are reset and the alarms are disabled.

STEP 2A

This is a computer, i.e., microprocessor 140, malfunction reset step which occurs every time a question (rhombus step) is asked. If the question comes back no, N, the computer checks itself. Since these "A" steps are the same they are not repeated hereafter but it will be understood that each time a question is asked and comes back no, N, the computer malfunction reset operation occurs and is located in the no, N, loop as shown.

STEP 3

This is a check to see if there is a valid "pack", i.e., a holder 18 in the apparatus 10 against a sensor 220 (FIG. 2). If there is, the yes, Y, answer will cause the program to continue to the next step in the sequence and if it is a no, N, answer it would cycle back and continue cycling.

STEP 4

This is a determination of the type of "pack" (holder 18) which is a "platelet pack".

STEP 5

Platelet collection is the procedure determined, all clamps are closed, all lights are turned off and the platelet light is turned on to indicate that this is a platelet collection procedure.

STEP 6

Here a check is made to see if everything is in proper order and if any one of a certain class of errors exists, e.g., overtemperature, motors not working properly, etc. If a yes, Y, answer occurs the computer determines which error is occurring. Each error has a code number and that number is displayed in the window 26. If everything is in proper order and there is no malfunction then a no, N, answer causes the program to continue to the next step.

STEP 7

Here the computer checks to see if the mode of operation is automatic or manual. If it is automatic, a yes, Y, answer occurs and the program continues to the next step.

STEP 8

In step 8 the prime light is flashed. Actually what happens is that a lamp by the prime button 42 flashes indicating to the operator that he should push the prime button 42.

STEP 9

The program now asks the question whether or not the prime button has been depressed. If it has, the program goes on to the next step. If not it will keep cycling.

Between steps 8 and 9 it will be understood that there will be a step 8A which will be in the same position in the loop as step 2A. However, in this step of checking for computer malfunction reset and also in subsequent "A" steps the program also checks to see if there is an abort. By an abort is meant one of the major malfunctions as was checked in Step 6 has occurred to abort operation of the apparatus 10. Thus Step 6 is now incorporated into the "A" steps. However, at Step 6 if a malfunction was sensed the apparatus 10 won't start whereas at step 8A (not shown) and all the other "A" steps where there is a check loop, instead of a "no start" the program will cause an abort or stopping of the operation of the apparatus 10. Repeating, the "A" step that is incorporated wherever there is a question asked and a feedback a loop is present, there will be a computer malfunction reset check and also there will be a check to see if certain malfunctions are occurring. If any of these malfunctions are occurring an abort signal will be generated to stop operation of the apparatus 10.

STEP 10

Assuming the prime button 42 has been depressed, valves #3 and #7 are closed and valves #1, #2, #4, #5 and #6 opened. Then the whole blood pump 20 is turned on and the plasma pump 22 is turned on. It is understood that saline was already connected to tubings 110 and 118. Before the pumps 20 and 22 are turned on, the ratio of the speeds for the pumps is set according to the formulas and operating procedures set forth above. The starting speed for pump 20, however, is an intermediate operating speed. At this step the plasma pump 20 is turned on and the incremental volume counter for the pumps 20 and 22 are started.

STEP 11

At step 11 the program senses whether or not the air bubble sensor 87 is working. If it is working and since there is air in the system at this stage it should sense air bubbles and a no, N, answer appears and an alarm is displayed. If the alarm is not displayed indicating that there are no air bubbles present or the sensor 87 is not working, and it is known there are air bubbles present, the program halts operation of the apparatus 10 because most likely there is a malfunction of the air bubble sensor or alarm logic. However, if the answer is a yes, Y, that air is present then the program goes on to an 11A step not shown and then to step 12.

STEP 12

A predetermined amount of fluid, e.g., 30 milliliters of fluid, is pumped by pump 20. When the computer finds from the incremental volume being measured by the whole blood incremental volume counter that 30 milliliters or some other given amount of fluid has been pumped by pump 20, then the program goes on to step 13.

STEP 13

At step 13, valve #1 and #2 are closed and the whole blood incremental counter is reset and started. Also, the plasma incremental counter is started.

STEP 14

Here the program checks to see what volumes are being processed by pump 20 and pump 22 until both of them have processed a desired volume of fluid. At that point the program goes on to step 15.

STEP 15

Now the speed of the rotor for the centrifuge device 14 is set, the centrifuge device 14 is turned on and the incremental volume counters are reset and started.

STEP 16

A predetermined volume of fluid is processed by pump 20 or 22 sufficient to remove bubbles.

STEP 17

At step 17 the hematocrit setting is read. This valve has been inserted into the program or an average hematocrit is used, such as a hematocrit of 42 and with that hematocrit set, the program sets the speed of pump 22. Of course, the speed of the pump 20 is first set at an initial value as determined above, e.g., 26 milliliters per minute and then the program automatically sets the speed of the pump 22 at some initial percentage of the speed of pump 20, e.g., $(1-0.42) \times$ speed of pump 20 or $0.58 \times V_{WB}$. Again, the initial speed of the whole blood pump 20 is set at some arbitrary number typically a speed between 25 and 35 milliliters per minute and the plasma pump 20 will have a speed that initially tracks the whole blood pump 20 at a ratio of 58/100. Also in this step the program resets and starts the whole blood incremental volume counter.

STEP 18

A given volume of fluid is now pumped by pump 20.

STEP 19

At step 19 the program checks the presure of the occluded vein sensor 63 and if that pressure is not within certain limits which have been predetermined an alarm code will be displayed. If the alarm code is not displayed the program goes on to the next step.

STEP 20

Here the occluded vein alarm pressure is set at a certain value minus a constant K. Step 20 is in a way combined with the check step at 19 because at 19 the operating pressure is determined and checked to see if it is within certain predetermined limits. Once that is determined, the actual pressure is determined and with a certain range needed below which the pressure can go, the alarm is set at that value minue the constant K. Then, if the pressure goes below the operating pressure value minus the constant K, an alarm code will be displayed and sensed and operation of the apparatus 10 is aborted.

STEP 21

At step 21 the program checks for a blocked line.

STEP 22

At step 22 a blocked line alarm value is set in the same way as in steps 19 and 20 except that with a certain pressure determined to be within limits a constant $K_2$ is added to that pressure value determined. If that value is exceeded an alarm code will be displayed and sensed and operation of the apparatus aborts.

STEP 23

At step 23 the program monitors the Hi-Lo pressure sensor 85 and determines whether or not the pressures are within certain limits for high and low pressure. The high pressure would be where the vein of, or the return needle 90 into, the donor is blocked. The low pressure would occur when a break occurs somewhere in the fluid circuit 16. If the pressures are beyond certain limits then the program will cause an alarm code to be displayed and sensed. Even though saline is now flowing through the system, pressures are checked with saline and those pressure values are used when connection is made to a donor.

STEP 24

At step 24, the high/low pressure limits or values are set and this is accomplished in the same manner as the pressure limits or values were determined in steps 19–22.

STEP 25

At step 25 valve #4 is closed and the whole blood incremental volume counter is reset and started.

STEP 26

A check for an occluded vein is made at this step.

STEP 27

A check for a certain volume of fluid flow, e.g., 5 milliliters into the system is made. With valve #4 closed an occluded vein condition is created and checked. If the occluded vein alarm code is displayed and sensed the program goes on to the next step. If the answer is a no, N, the system is stopped.

STEP 28

At step 28 valve #4 is opened. Also the whole blood incremental volume counter is reset and started.

STEP 29

A check is made here to determine if a certain volume of whole blood has been pumped. Typically, 5 milliliters are pumped to stabilize the system in view of the opening and closing of valve #4.

STEP 30

At step 30 valve #5 is closed.

STEP 31

Here a check is made to see if 15 milliliters of fluid has been pumped by the whole blood pump 20 and when that has occurred the program goes on to step 32.

STEP 32

At step 32, valve #5 is closed, and flow of saline back to container 108 is blocked. The high pressure alarm code will be displayed and sensed. If a high pressure alarm is sensed it is assumed that the low pressure alarm works also. If a high alarm is sensed the program goes on to step 33.

STEP 33

At step 33, both of the pumps 20 and 22 are stopped, valves #1, #2, #3, #4, #5 and #6 are opened and valve #7 is closed. At this step a run light is flashed which means that the functions in step 33 have been performed. That indicates that the system, apparatus 10, is reading for a "run".

In steps 19 through 32, if an error is detected, the operation of apparatus 10 is halted with the lamp for resume button 45 flashing. If the cause of the error is corrected and the resume button 45 pushed, the program starts over at step 19 regardless of where the error was detected.

RUN

STEP 34

At this step the tubings 54 and 82 are connected to the donor 52. The flashing run light indicates that the connections to the donor 52 can be made. Then the run button 43 is depressed and the platelet run protocol or program is started. The computer 140 now asks the question whether or not the run button has been pushed. Once the run button 43 has been pushed after a donor 52 is connected to the system (fluid circuit 16), the program goes on to step 35.

STEP 35

At step 35 the run light has stopped flashing and now the run light is on solid. At this step, valves #1, #2, #5 and #6 are opened and valves #3, #4 and #7 are closed. The whole blood and plasma incremental volume counters are reset and started. Also the alarms are stopped and reset. Simply, at step 35 any alarm in the system or any counter in the system is reset. Then the whole blood pump 20 is turned on, the plasma pump 22 is turned on, and the occluded vein sensor 63 is enabled. Also, underspeed error alarm sensors are enabled. At this time also the elapsed time counter 148 is started and the total volume counter (displayed at 155) is started. It will be understood that the initial starting speed for pump 20 has already been established by the program, e.g., 26 milliliters per minute, as well as the ratio established by the program, e.g., 0.58/100.

STEP 36

Here a check of whole blood flow is made to determine when the system has stabilized. When a yes, Y, answer is sensed, the program goes on to step 37.

STEP 37

At step 37, valve #5 is closed and valve #3 is opened. The blocked vein sensor 85 is enabled to see if the entry vein in the donor is blocked. All sensors 63, 65 and 85 are enabled. Also the spill detector device 76 is enabled and air bubble sensor 87 is enabled.

STEP 38

At step 38 the question is asked whether plasma is going to be collected. If the answer is yes, Y, the program goes on to step 39. Otherwise, if the answer is a no, N, the program resumes at step 40.

STEP 39

At step 39 a check "flag", i.e., for scanning the program to see if plasma is going to be collected, is reset. Valve #6 is closed. Valve #7 is opened and the plasma incremental volume counter is started.

STEP 40

Step 40 represents the beginning of the spillover routine, i.e., spillover of red blood cells into tubing 74 and loop 75 is sensed by device 76. At step 40 a check is made to see if 120 milliliters have been processed or if there was a spillover. If 120 milliliters has been processed without a spillover the program goes to step 41, otherwise the program goes to step 42.

STEP 41.

At step 41 the pump 22 speed is increased 1 milliliter per minute with pump 20 speed increased proportionately. The whole blood counter is reset and the program returns to step 40.

STEP 42

If a spillover occurs the plasma pump 22 is stopped and reversed and 10 milliliters of plasma mixed with spilled-over red blood cells is pumped back into the blood bag 66. Then the direction of pump 22 is returned to forward and the program advances to step 43.

STEP 43

At step 43, the whole blood pump 20 speed is decreased by 1 milliliter per minute and, of course, the plasma pump 22 speed will now be decreased in speed proportionately by the ratio. Then the 120 milliliter counter of whole blood is reset and the program goes to step 44.

STEP 44

A check is made to see if a spillover occurred or if 120 milliliters processed. If 120 milliliters were processed without a spillover the program goes to step 45. Otherwise the program goes to step 46.

STEP 45

The plasma pump 22 speed is increased by 0.25 milliliters per minute. The whole blood counter is reset and the program returns to step 44.

STEP 46

If a spillover occurs the plasma pump 22 is stopped and reversed and 10 milliliters of plasma mixed with spilled-over red blood cells is pumped back into the blood bag 66. Then the direction of pump 22 is returned to forward and the program advances to step 47.

STEP 47

Next the plasma pump 22 speed is decreased 0.25 milliliters per minute and the whole blood counter is reset and the program goes to step 48.

STEP 48

A check is made to see if a spillover has occurred or if the end point has been reached. If a spillover occurs the program goes to step 49. Otherwise the program goes to step 50.

STEP 49

If a spillover occurs the plasma pump 22 is stopped and reversed and 10 milliliters of plasma mixed with spilled-over red blood cells is pumped back into the blood bag 66. Then the direction of pump 22 is returned to forward and the program advances to step 47.

While the program is in steps 40-49 it is also checking for errors some of which have been mentioned above at the "A" (2A) steps; and volume counters are checked for the various processings of fluid to determine how much plasma or whole blood has been processed. If plasma was collected, i.e., if step 39 occurred, a check is made to see if the appropriate amount of plasma has been collected. When that occurs valve #6 is opened and valve #7 is closed.

STEP 50

At step 50 valve #1 is closed and the volume process display is stopped at the desired volume of 3 liters.

STEP 51

At this step, the lamp for reinfuse button 44 is caused to flash on and off. Button 44 is now pushed to reinfuse. Then valve #4 is opened and saline is allowed to flow into the system. Now the moving of whole blood through the system is continued unit end point plus some quantity of say 50 milliliters has been reached.

STEP 52

Step 52 checks to see if 50 milliliters of saline has been pumped to purge the whole blood that is in the system (fluid circuit 16) or almost all of it out of the system and back into the donor. Of course, also while this is being checked, an "A" step is occurring for error check and abort check, i.e., all of those checks which were done previously. Once this has occurred the protocol or program goes on.

STEP 53

Here the whole blood pump 20 and the plasma pump 22 are stopped and valves #2, #3 and #4 are closed and valve #5 opened. Also the centrifuge rotor is stopped. Valve $5 is opened since, when the rotor is stopped there is a pressure buildup in the whole blood bag and the platelet bag and that pressure has to be relieved into the saline bottle which is a collapsable flexible bottle.

STEP 54

Here the program checks to see if the rotor is stopped or nearly under 50 rpm.

STEP 55

At step 55 valve #5 is closed. All are now closed and the run light is off. A code number appears and perhaps an audible signal is actuated to indicate that the run is finished.

From the foregoing description it will be apparent that the method and apparatus 10 of the present invention have a number of advantages some of which have been described above and others of which are inherent in the invention. Also, obvious modifications can be made to the method and apparatus of the present invention without departing from the teachings of the invention. For example, instead of centrifuging bags 66 and 80 in the one centrifuge device 14, bag 66 can be centrifuged in the centrifuge device 14 and the bag 80 can be centrifuged in another centrifuge device so that different speeds of rotation and different g forces can be applied to the bags 66 and 80 to obtain a desired separation of blood components in, and sedimentation of blood particles in the bags 66 and 80.

We claim:

1. A method for separating blood components from whole blood including the steps of: withdrawing whole blood from a donor and passing the same through a fluid system; said passing of whole blood through the system including passing the whole blood through a first compartment for centrifuging of the whole blood therein; centrifuging the whole blood to cause separation of the whole blood into components thereof in the first compartment; withdrawing one fluid component out of the first compartment for monitoring the one fluid component and then moving that one compartment through a second compartment for the centrifuging of the one component therein while passing the remaining blood fluid through the first compartment; centrifuging the one fluid component in the second compartment to cause sedimentation of particles therein; recombining the fluid passed through the second compartment with the blood fluid passed through the first compartment; returning the recombined blood fluid to the donor; monitoring the withdrawn one fluid component and sensing withdrawal of other components with the one fluid component; stopping and then reversing movement of the one fluid component when a mixture is sensed to return any mixture of components to the first compartment for separation of the blood components therein; adjusting the difference in rates of withdrawal of whole blood and the one component in response to said sensing of a mixture of components; repeating the above steps until a desired volume of whole blood has been processed followed by isolating and removing the second compartment from the system.

2. The method according to claim 1 wherein the one component is platelet rich plasma and the particles are platelets.

3. The method accoarding to claim 2 wherein the ratio of the difference in rates of withdrawal of whole blood and platelet rich plasma is caused to approach the following formula:

$$\frac{V_{BI}}{V_{BI} - V_{PRP}} = \frac{\text{HEMATOCRIT}_{(BLOOD\ FLUID\ OUT)}}{\text{HEMATOCRIT}_{(BLOOD\ IN)}}$$

where:

$V_{BI}$=volumetric flow in milliliters per minute of whole blood in, $V_{PRP}$=volumetric flow in milliliters per minute of platelet rich plasma withdrawn from the first container, HEMATOCRIT$_{(BLOOD\ FLUID\ OUT)}$=concentration of red blood cells (by volume) per milliliter of blood fluid passing out of the first compartment, HEMATOCRIT$_{(BLOOD\ IN)}$=concentration of red blood cells (by volume) per milliliter of fluid of the whole blood in.

4. The method according to claim 2 wherein said withdrawal of whole blood is initially started at a volumetric rate of 26 milliliters per minute and increased periodically by an increment of one milliliter per minute, a period being determined by the time it takes to move a given volume of the system through the system, until red cells are sensed in the platelet rich plasma.

5. The method according to claim 2 wherein the platelet rich plasma is initially withdrawn from the first compartment at a volumetric rate which is equal to $$(1-\text{HEMATOCRIT}_{(BLOOD\ IN)}) \times V_{BI}$$

where: $V_{BI}$=volumetric flow in milliliters per minute of whole blood in.

6. The method according to claim 2 wherein the rate of withdrawal of platelet rich plasma is increased 0.25 milliliters per minute each time a given volume of blood has been passed through the system without a spillover of red blood cells into the platelet rich plasma being sensed until such a spillover is sensed, whereupon, after a sufficient volume of platelet rich plasma mixed with red blood cells is returned to the first compartment, withdrawal of platelet rich plasma is resumed with the rate of withdrawal of platelet rich plasma decreased by an increment of 0.25 milliliters per minute.

7. The method according to claim 2 including the step of collecting a portion of the plasma passed through the second compartment prior to recombining the plasma passed through the second compartment with the blood fluid passed through the first compartment.

8. The method according to claim 2 wherein the adjustment in the difference in rates of withdrawal of whole blood and platelet rich plasma, in response to said sensing of a mixture of components which comprises a mixture of red blood cells with platelet rich plasma after the withdrawal of platelet rich plasma is stopped and a volume of platelet rich plasma mixed with red blood cells large enough to ensure complete return of the platelet rich plasma mixed with red blood cells is returned to the first compartment, is effected by reducing the rate of withdrawal of platelet rich plasma by a predetermined volumetric flow increment.

9. The method according to claim 8 wherein said predetermined incremental reduction in the volumetric flow rate of withdrawal of platelet rich plasma is 0.25 milliliters per minute.

10. The method according to claim 1 wherein the centrifuging in the first and second compartments occurs at a "g" force of between 150 and 600 g's.

11. The method according to claim 10 wherein the centrifuging takes plate in the first and second compartments at approximately 285 g's.

12. The method according to claim 1 wherein the whole blood is withdrawn from the donor at a volumetric rate of between 15 and 50 milliliters per minute.

13. The method according to claim 12 wherein whole blood is withdrawn from the donor at a volumetric rate of 30±5 milliliters per minute.

14. The method according to claim 1 wherein a predetermined amount of anti-coagulant is added to the whole blood withdrawn from the donor.

15. The method according to claim 1 wherein the centrifuging takes place in a centrifuge device and said one fluid component is withdrawn not only from said first compartment but also out of the centrifuge device for the monitoring of the one fluid component outside of the centrifuge device and then is moved back into the centrifuge device and into the second compartment therein.

16. The method according to claim 1 including the steps of monitoring the pressure of the whole blood withdrawn from the donor for the purpose of sensing occlusions in the bloodstream.

17. The method according to claim 1 including the step of monitoring the pressure of the recombined blood fluid which is returned to the donor to ensure against occlusions in the path to the donor when a high pressure is sensed and to learn of leaks in the system if a low pressure is sensed.

18. The method according to claim 1 including the step of passing the recombined blood fluid through a bubbletrap to ensure against passing air bubbles to the donor.

19. The method according to claim 1 including the step of passing saline solution through the system prior to withdrawing blood from the donor.

20. The method according to claim 19 wherein saline solution is passed through the system after collecting a given amount of particles to ensure return of the blood fluid in the system to the donor.

21. The method according to claim 1 wherein the rate of withdrawal of whole blood from the donor is increased a predetermined amount each time a volume capacity of the system is processed with the ratio of the rate of movement of the one fluid component to the rate of withdrawal of whole blood being maintained at a fixed ratio until a mixture of components is sensed.

22. The method according to claim 21 wherein said predetermined amount is one milliliter per minute.

23. The apparatus according to claim 21 wherein said third coupling means includes a loop which extends out of and is positioned exterior of said centrifuge device and said monitoring means is associated with said loop and is located exterior of said centrifuge device.

24. The apparatus according to claim 23 wherein said moving means includes a peristaltic pump which engages said loop.

25. The apparatus according to claim 24 wherein said loop has a light transmitting portion and said monitoring and sensing means includes an optical device which is situated adjacent said portion of said loop exterior of said centrifuge device and which is operable to sense another blood component in said loop.

26. The method according to claim 21 wherein, when a mixture of components is sensed, the movement of the one fluid component is stopped and then reversed until a predetermined incremental amount of the one fluid component mixed with another component is returned to the first comparment.

27. The method according to claim 26 wherein said icremental amount of the one fluid component is approximately ten milliliters.

28. The method according to claim 26, wherein, after a first sensing of a mixture of components, the rate of withdrawal of whole blood is reduced a predetermined amount.

29. The method according to claim 28 wherein said reduced predetermined amount is one milliliter per minute.

30. The method according to claim 28 wherein, after the rate of withdrawal of whole blood has been reduced, the rate of movement of the one fluid component is periodically increased by a predetermined amount until another mixture of components is sensed, whereupon, the rate of movement of the one fluid component is decreased by a certain amount.

31. The method according to claim 30 wherein said amount of increased rate of movement is .25 milliliters per minute.

32. The method according to claim 30 wherein said decreased certain amount is 0.25 milliliters per minute.

33. An apparatus for separating blood components from whole blood comprising: a centrifuge device, a first, whole blood receptacle situated in said device and having an inlet and at least a first outlet and a second outlet, said first outlet being located adjacent a zone where one blood component congregates and said second outlet being located adjacent a zone where another blood component congregates when the centrifuge device is operated, a second receptacle situated in said device and having an inlet and an outlet, means exterior of said device for withdrawing whole blood from a donor, first means coupling said withdrawing means to said first receptacle inlet, second means coupling said first outlet of said first receptacle to the donor, third means coupling said second outlet of said first receptacle to said inlet of said second receptacle, fourth means for coupling said outlet of said second receptacle to said second coupling means for recombining the one blood component with the blood fluid from said first receptacle, means for moving the one blood component from said first receptacle to said second receptacle in which particles are separated from the one blood component by centrifugal force and means for monitoring the one blood component fluid flow in said third coupling means and for sensing when another blood component is present in said third coupling means, means for stopping and then reversing operation of said moving means in response to the sensing of the presence of a mixture of blood components to return the mixture to said first receptacle for separation of the blood components therein, and means for adjusting the relative rates of fluid movement of said withdrawing means and said moving means in response to the sensing of the other blood component.

34. The apparatus according to claim 33 including an air bubble trap/filter coupled to said fourth coupling means between said first receptacle and the donor for filtering out any bubbles which may become entrapped in the fluid path of the apparatus to ensure against the injection of air bubbles in the donor.

35. The apparatus according to claim 33 wherein said first coupling means includes a flexible tubing and said withdrawing means includes a peristaltic pump which is situated exterior of said centrifuge device and which engages said tubing for moving fluid through said tubing.

36. The apparatus according to claim 35 including a pressure sensor coupled to said tubing between the donor and said pump for sensing a pressure drop below a predetermined level indicating an occluded vein in the donor and causing stoppage of the operation of said apparatus in response to the pressure drop.

37. The apparatus according to claim 35 including a pressure sensor coupled to said tubing between said pump and said centrifuge device for sensing a pressure rise above a predetermined level indicating a blockage of fluid flow through the apparatus and causing stoppage of the operation of said apparatus in response to the pressure rise.

38. The apparatus according to claim 33 including a high and low pressure sensor coupled to said third coupling means between the outlet of said second receptacle and the donor and being operable upon sensing a high pressure above a predetermined level indicating an occluded vein in the donor, or a low pressure below a predetermined level indicating a leak in the fluid path through the apparatus to cause stoppage of the operation of said apparatus.

39. The apparatus according to claim 38 including a sensing device associated with said air bubble trap/filter for sensing when air bubbles are present in the fluid path of the system and filtered out by the air bubble trap/filter.

40. The apparatus according to claim 39 including a source of anti-coagulant and fifth coupling means for coupling said source of anti-coagulant to said first coupling means.

41. The apparatus according to claim 40 including first valve means associated with said first coupling means and operable to open and close said first coupling means, second valve means associated with said fifth coupling means and operable to open and close said coupling means, third valve means associated with said fourth coupling means and operable to open and close said fourth coupling means and control means for controlling the opening and closing of the first, second and third valve mean.

42. The apparatus according to claim 41 including a source of saline solution, sixth coupling means for coupling said source of saline solution to said first coupling means, fourth valve means associated with said sixth coupling means for controlling coupling of said source of saline solution to said first coupling means, seventh coupling means for coupling said source of saline solution with said fourth coupling means, and fifth valve means associated with said seventh coupling means for opening and closing said seventh coupling means, said control means being operable to control operation of said fourth and fifth valve means for passing saline solution through the fluid path of said apparatus.

43. The apparatus according to claim 43 including a third receptacle situated exterior of said centrifuge device for collecting some of the blood fluid of the one blood component, eighth coupling means for coupling said third receptacle to said third coupling means, sixth valve means associated with said third coupling means and situated between the junction of said eighth coupling means with said third coupling means and the junction of said third coupling means with said fourth coupling means, and seventh valve means associated with said eighth coupling means for opening and closing said eighth coupling means and said control means being operable to control operation of said sixth and seventh valve means.

44. The apparatus according to claim 43 including an air bubble trap/filter coupled to said fourth coupling means between said first receptacle and the donor for filtering out any bubbles which may become entrapped in the fluid path of the apparatus to ensure against the injection of air bubbles in the donor, a sensing device associated with said air bubble trap/filter, said first coupling means including a first flexible tubing, said withdrawing means including a first peristaltic pump which is situated exterior of said centrifuge device and which engages said tubing for moving fluid through said tubing, a first pressure sensor coupled to said first tubing between the donor and said first pump for sensing a pressure drop below a predetermined level indicating an occluded vein in the donor and causing stoppage of the operation of said apparatus in response to the pressure drop, a second pressure sensor coupled to said first tubing between said pump and said centrifuge device for sensing a pressure rise above a predetermined level indicating a blockage of fluid flow through the apparatus and causing stoppage of the operation of said apparatus in response to the pressure rise, a third high and low pressure sensor coupled to said third coupling means between the outlet of said second receptacle and the donor and being operable upon sensing a high pressure above a predetermined level indicating an occluded vein in the donor, or a low pressure below a predetermined level indicating a leak in the fluid path through the apparatus to cause stoppage of the operation of said apparatus, said third coupling means includes a loop which extends out of and is positioned exterior of said centrifuge device, said moving means including a second peristlatic pump which engages said loop which includes a light transmitting section and said monitoring and sensing means including an optical device which is situated adjacent said section of said loop exterior of said centrifuge device and which is operable to sense another blood component in said loop.

45. The apparatus according to claim 44 wherein said control means includes a microprocessor and associated control circuitry for controlling operation of said apparatus, said microprocessor and associated control circuitry being coupled to said sensors, said pumps, said valves, and said centrifuge device to provide semi-automatic operation of said apparatus.

46. The apparatus according to claim 41 including a third receptacle for collecting some of the blood fluid of the one blood component situated exterior of said centrifuge device and sixth coupling means coupling said third receptacle with said third coupling means.

47. The apparatus according to claim 46 including first valve means associated with said first coupling means and operable to open and close said first coupling means, second valve associated with said fifth coupling means and operable to open and close said fifth coupling means, third valve means associated with said fourth coupling means and operable to open and close said fourth coupling means, fourth valve means associated with said sixth coupling means, fifth valve means associated with said third coupling means and situated between the junction of said sixth coupling means and said third coupling means and the junction of said third coupling means and said fourth coupling means and control means for controlling the opening and closing of the first, second, third, fourth, and fifth valve means.

48. The apparatus according to claim 40 including second withdrawing means operated synchronously with said first withdrawing means for withdrawing anti-coagulant from said source of anti-coagulant for mixing with the whole blood flowing through said first coupling means.

49. The apparatus according to claim 48 wherein said first and second withdrawing means comprise a peristaltic pump, said first coupling means include a tubing, a section of which engages said peristaltic pump, said fifth coupling means include a tubing, a section of which engages said peristaltic pump, and said two tubings have different diameters so that anti-coagulant is mixed with whole blood at a predetermined ratio of anti-coagulant to whole blood.

50. The apparatus according to claim 30 including a source of saline solution and first valve and coupling means for coupling said source of saline solution to said first coupling means and second valve and coupling means for coupling said source of saline solution to said fourth coupling means whereby saline solution can be passed through the fluid path of the apparatus.

51. A method for separating blood components from whole blood including the steps of: withdrawing whole blood from a donor and passing the same through a fluid systen; said passing of whole blood through the system including passing the whole blood through a first compartment in a centrifuge device; centrifuging the whole blood in the centrifuge device to cause separation of the whole blood into components thereof in the first compartment; withdrawing one fluid component out of the first compartment and out of the centrifuge device for monitoring the one fluid component and then moving that one component back into the centrifuge device through a second compartment in the centrifuge device while passing the remaining blood fluid through the first compartment; centrifuging the one fluid component in the second compartment to cause sedimentation of particles therein; recombining the fluid passed through the second compartment with the blood fluid passed through the first compartment; returning the recombined blood fluid to the donor; monitoring the withdrawn one fluid component outside of the centrifuge device and sensing withdrawal and mixing of other components with the one fluid component; stopping and then reversing movement of the one fluid component when a mixture is sensed to return any mixture of components to the first compartment for separation of the blood components therein; adjusting the difference in rates of withdrawal of whole blood and the one component in response to said sensing of a mixture of components; repeating the above steps until a desired volume of whole blood has been processed followed by isolating and removing the second compartment from the system.

52. A method for separating blood components from whole blood including the steps of: withdrawing whole blood from a donor and passing the same through a fluid system; said passing of whole blood through the system including passing the whole blood through a first compartment in a centrifuge device; centrifuging the whole blood in the centrifuge device to cause separation of the whole blood into platelet rich plasma and red blood cells in the first compartment; withdrawing platelet rich plasma from the first compartment and out of the centrifuge device for monitoring the platelet rich plasma and then moving the platelet rich plasma back into the centrifuge device and through a second compartment in the centrifuge device while passing the remaining blood fluid through the first compartment; centrifuging the platelet rich plasma in the second compartment to cause sedimentation of platelets therein; recombining the plasma passed through the second compartment with the blood fluid passing through the first compartment; returning the recombined blood fluid to the donor; monitoring the withdrawn platelet rich plasma outside of the centrifuge device and sensing withdrawal and mixing of red blood cells with platelet rich plasma, stopping and then reversing movement of the platelet rich plasma when a mixture is sensed to return any mixture of platelet rich plasma and red blood cells to the first compartment for separation of the blood into platelet rich plasma and red blood cells in the first compartment; adjusting the difference in rates of withdrawal of whole blood and the platelet rich plasma in response to said sensing of a mixture of components; repeating the above steps until a desired volume of whole blood has been processed followed by isolating and removing the second compartment from the system.

53. An apparatus for separating blood components from whole blood comprising: a centrifuge device, a first, whole blood receptacle situated in said device and having an inlet and at least a first outlet and a second outlet, said first outlet being located adjacent a zone where one blood component congregates and said second outlet being located adjacent a zone where another blood component congregates when the centrifuge device is operated, a second receptacle situated in said device and having an inlet and an outlet, means exterior of said device for withdrawing whole blood from a donor, first means coupling said withdrawing means to said first receptacle inlet, second means coupling said first outlet of said first receptacle to the donor, third means coupling said second outlet of said first receptacle to said inlet of said second receptacle, fourth means for coupling said outlet of said second receptacle to said second coupling means for recombining the one blood component with the blood fluid from said first receptacle, and said third coupling means including a loop which extends out of and is positioned exterior of said device, means for moving the one blood component from said first receptacle to said second receptacle in which particles are separated from the one blood component by centrifugal force and means exterior of said centrifuge device for monitoring the one blood component fluid flow in said loop and for sensing when another blood component is present in said loop, means for stopping and then reversing operation of said moving means in response to the sensing of the presence of a mixture of blood components in said loop to return the mixture to said first receptacle for separation of the blood component therein, and means for adjusting the relative rates of fluid movement of said withdrawing means and said moving means in response to the sensing of the other blood component.

54. An apparatus for separating platelets from whole blood comprising: a centrifuge device, a first, blood separation receptacle situated in said device and having an inlet and at least a first outlet and a second outlet, said first outlet being located adjacent a zone where red blood cells congregate and said second outlet being located adjacent a zone where platelet rich plasma congregates when the centrifuge device is operated, a second platelet collection receptacle situated in said device and having an inlet and an outlet, said second receptacle being arranged so that sedimentation of platelets on the walls of the second receptacle will take place when the centrifuge device is rotated, means exterior of said device for withdrawing whole blood from a donor, first means coupling said withdrawing means to said first receptacle inlet, second means coupling said first outlet of said first receptacle to the donor, third means coupling said second outlet of said first receptacle to said inlet of said second receptacle, fourth means for coupling said outlet of said second receptacle to said second coupling means for recombining platelet poor plasma with the blood fluid from said first receptacle, and said third coupling means including a loop which extends out of and is positioned exterior of said device means for moving platelet rich plasma from said first receptacle to said second receptacle in which platelets are separated from the plasma by centrifugal force and means exterior of said centrifuge device for monitoring the fluid flow of platelet rich plasma in said loop and for sensing when red blood cells are present in said loop, means for stopping and then reversing operation of said moving means in response to the sensing of the presence of a mixture of red blood cells with platelet rich plasma in said loop to return the mixture to said first receptacle for the separation of red blood cells from platelet rich plasma in said first receptacle and means for adjusting the relative rates of fluid movement of said withdrawing means and said moving means in response to the sensing of a mixture of red blood cells with platelet rich plasma.

* * * * *